United States Patent [19]

Williams et al.

[11] Patent Number: 4,992,522
[45] Date of Patent: Feb. 12, 1991

[54] POLYMER COMPATIBILIZERS

[75] Inventors: David A. Williams, Gansevoort; Paul R. Willey, Clifton Park; Brian J. Ward, Easton, all of N.Y.

[73] Assignee: General Electric Co., Waterford, N.Y.

[21] Appl. No.: 412,247

[22] Filed: Sep. 25, 1989

[51] Int. Cl.$^5$ ............................................. C08G 77/20
[52] U.S. Cl. ................................. 528/32; 556/469; 556/450; 528/38; 528/33
[58] Field of Search ............... 556/469, 450; 528/32, 528/38, 33

[56] References Cited

U.S. PATENT DOCUMENTS

| | | | |
|---|---|---|---|
| 4,150,010 | 4/1979 | Itoh et al. | 260/37 |
| 4,201,698 | 5/1980 | Itoh et al. | 266/3 |
| 4,365,042 | 12/1982 | Cooper et al. | 525/68 |
| 4,599,367 | 7/1986 | Bauman et al. | 528/32 |
| 4,650,849 | 3/1987 | Nishimura et al. | 528/26 |
| 4,659,851 | 4/1987 | Plueddemann | 556/431 |
| 4,847,332 | 7/1989 | Yu | 528/15 |

OTHER PUBLICATIONS

A New High Performance Elastomer Composition by J. M. Mitchell & T. Wada paper No. 23 presented at the 127th Meeting of the Rubber Division, American Chemical Society Los Angeles, CA Apr. 23–26, 1985.

*Primary Examiner*—Melvyn I. Marquis
*Assistant Examiner*—Karen Hellender

[57] ABSTRACT

There is provided a compatibilizer comprised of essentially linear molecules terminated with an unsaturated radical on one end and a condensable radical on the other end and represented by general formula:

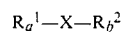

$$R_a^1-X-R_b^2$$

wherein X is a tetravelent organic or silicon containing group; $R^1$ is selected from the group consisting of $C_{1-12}$ alkyl and $C_{2-12}$ alkenyl; $R^2$ is a $C_{1-10}$ alkylamine; "a" is less than 4 and greater than or equal to 1; "b" is less than 4 and greater than or equal to 1; and a+b is equal to 4.

8 Claims, No Drawings

POLYMER COMPATIBILIZERS

BACKGROUND OF THE INVENTION

Different polymer materials exhibit varied and different physical characteristics. It is often the case that a polymer has excellent physical properties in one area but has poor physical properties in other areas. As an example of this consider silicone rubber. While silicone rubber has excellent heat resistance, it also has poor oil and abrasion resistance in comparison to organic polymers.

It would seem then that a simple solution would be to mechanically blend different polymers together, each having complementary physical property profiles, so that the resultant polymer blend would exhibit the superior physical properties of each component in the blend. However, the reality of the situation is that such polymer blends usually exhibit inferior physical properties.

One reason for this is the fact that polymers may have different curing mechanisms. That is, whether the polymer crosslinks by hydrosilation, condensation, etc., will determine the rate at which the polymer will react to final cure. If two or more dissimilar polymers are present and each of them cures independently of the others the result will be regions where the polymer blend is rich in one polymer and deficient in the other polymer(s).

On the other hand, if the cure mechanism is the same for two or more polymers the polymers will intercrosslink at the same rate with each other during final cure. The result is an interpenetrating polymer network that is homogeneous in each reactant.

Therefore, it is theorized that if polymers with different curing mechanisms can be compatibilized by modification of the curing reaction in one of the polymers it will be possible to covalently bond two or more dissimilar polymer materials to take advantage of the superior physical properties in each polymer. Such a compatibilizer, then, will adapt one polymer material to chemically combine with another.

In addition, compatibility is also determined by the nature of the polymers themselves. That is, when organic and silicone polymers are blended together phase separation may occur between the organic and silicone materials. Therefore, it is also theorized that dissimilar polymer components in a composition should be compatibilized by covalently bonding to one of them a material which avoids this phase separation.

U.S. Pat. No. 4,650,849 (Nishimuar et al.) discloses a photosensitive curable resin composition comprising an organosilicon compound having amino and vinyl functional groups; a tetracarboxylic acid anhydride, and a diamino compound.

U.S. Pat. No. 4,659,851 (Plueddemann) discloses organosilicon compounds that will cohesively bond polyorganosiloxane elastomers and resins to inorganic and organic substrates. The organosilicon compounds comprise alkoxy, hydroxy, and vinyl functional siloxanes and silanes.

U.S. Pat. No. 4,365,042 (Cooper et al.) discloses compatibilized compositions containing polyphenylene oxide and EPDM-silicone rubber using fumed silica filler as the compatibilizer.

U.S. Pat. No. 4,201,698 (Itoh et al.) discloses the use of an organopolysiloxane having aliphatically unsaturated functional groups and mercapto functional groups to react with a natural rubber or a synthetic rubber.

U.S. Pat. No. 4,150,010 (Itoh et al.) discloses the use of an organopolysiloxane having mercapto functional groups to react with an ethylene-propylene copolymeric elastomer.

The compatibilization of EPDM rubber with an elastomeric organopolysiloxane by the use of silica filler is described by Mitchell and Wada, *A New Performance Elastomer Composition*, American Chemical Society, 127th Meeting of the Rubber Division, Los Angeles, Calif., Apr. 23–26, 1985.

It is an object of this invention to produce a polymer alloy compatibilizer which can be used to compatibilize one polymer so that it can then be reacted with a second polymer.

It is further an object of this invention to provide a process for producing polymer alloy compatibilizers.

Other objects will become apparent upon reading this specification.

SUMMARY OF THE INVENTION

According to the objects of this invention there is provided a compatibilizer comprised of essentially linear molecules terminated with an unsaturated radical on one end and a condensable radical on the other end and represented by the general formula:

$$R_a^1 - X - R_b^2$$

wherein X is a tetravalent organic or silicon containing group; $R^1$ is selected from the group consisting of $C_{1-12}$ alkyl and $C_{2-12}$ alkenyl; $C_{2-12}$ alkynyl; $R^2$ is a condensable functional group: "a" is less than 4 and greater than or equal to 1; "b" is less than 4 and greater than or equal to 1., and a+b is equal to 4.

DETAILED DESCRIPTION OF THE INVENTION

The compatibilizer contemplated by this invention is comprised of essentially linear molecules terminated with an unsaturated radical on one end and a condensable radical on the other end and represented by the general formula:

$$R_a^1 - X - R_b^2$$

wherein X, $R^1$, $R^2$, "a", and "b" are as previously defined. The purpose of such a material is to compatibilize or adapt the reaction mechanism of a polymer that crosslinks by either a free radical addition reaction or a hydrosilation reaction with another polymer that crosslinks by a condensation reaction.

The group, X, may be any tetravalent organic or silicon containing group. It is preferable, however, that both "a" and "b" each equal 2. It is also preferable that one $R^1$ group be $C_{2-12}$ alkenyl and that one $R^2$ group be a condensable radical with the remaining groups being $C_{1-12}$ alkyl groups. This embodiment may be represented by the formula:

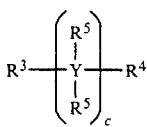

wherein $R^3$ is $C_{2-12}$ alkenyl; $R^4$ is a condensable functional group; $R^5$ is selected from the class consisting of hydrogen and $C_{1-12}$ alkyl; and "c" a number from 1 to about 100.

The group, $—(R_2{}^5)Y—$, is any difunctional organic or silicone containing group. Examples of this class includes alkylene such as methylene, ethylene, propylene, isopropylene, etc.; and oxyalkylene such as oxymethylene, oxyethylene, oxypropylene, etc. However, it is preferable that the group, $—(R_2{}^5)Y—$, consist of difunctional siloxane units of the formula:

$$—(R_2{}^5)Si—O—$$

which may be more reactive with silicon containing polymers.

Thus, the compatibilizer may be preferably defined as a difunctional organsiloxane that is represented by the formula:

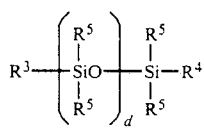

wherein $R^3$, $R^4$, $R^5$ are as previously defined and "d" is a number of from 0 to about 99.

The radical $R^5$ is defined as $C_{1-12}$ alkyl, but is preferably methyl.

The radical $R^3$ is any monofunctional hydrocarbon containing up to 12 carbon atoms and has some degree of ethylenic unsaturation. It is preferable, however, that the unsaturation occur at the terminal end of the radical. Thus, it is preferable that $R^3$ be selected from the group consisting of $CH_2=CH—$ and $CH_2=CH—(CH_2)_n—$ where "n" is a number of from 1 to 10. Of these radicals, the most preferable is vinyl, $CH_2=CH—$.

The radical $R^4$ is any group which will undergo a condensation reaction. Examples of such radicals include halogens such as chlorine and bromine; halogenated alkyls such as 3,3,3-trifluoropropyl; $C_{1-12}$ alkoxy such as methoxy, ethoxy, etc.; hydroxy; amine; $C_{1-10}$ alkylamine., mercaptan; and $C_{1-10}$ alkylmercaptan.

Preferably, $R^4$ consists of a $C_{1-10}$ alkylamine. More preferably, $R^4$ is propylamine. Further, while the amine may be either primary, secondary, or tertiary, it is preferable that primary amines be used.

The degree of polymerization, "d", may be any number between 0 and 99. However, it is preferred that "d" range from 1 to about 30. One preferred embodiment would have "d" equal to 1. Another preferred embodiment would have "d" range from 1 to about 30 and have an average value of from 9 to about 12.

Thus, one preferred embodiment of the compatibilizer contemplated by this invention is 1-(gamma amino)-propyl-3-vinyl tetramethyldisiloxane and is represented by the formula:

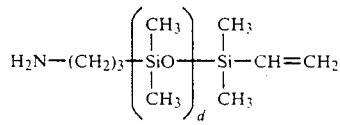

Another preferred embodiment of this invention, where "d" ranges from 1 to 30 and averages from about 9 to about 12, is represented by the formula:

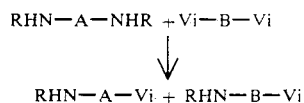

where "d" is as defined above.

The process for producing the preferred compatibilizer of this invention involves equilibrating a diamine with a divinylsiloxane compound in the presence of tetraalkylammonium hydroxide. Such a reaction is represented as follows:

$$RHN—A—NHR + Vi—B—Vi$$
$$\downarrow$$
$$RHN—A—Vi + RHN—B—Vi$$

wherein R is hydrogen or a lower alkyl that is preferably methyl, ethyl, or propyl. The groups A and B may be different but it is preferred that they be the same.

The diamines useful in this invention are those taught in U.S. Pat. Nos. 4,584,393 (Webb) and 4,631,346 (Webb), hereby incorporated by reference such as bis-(aminoalkyl)disoloxanes. These diamines may be further equilibrated with cyclic tetramethylsiloxane to yield diamines of higher molecular weight.

The divinylsiloxanes that are useful in producing the compatibilizers of this invention include divinyltetramethyldisiloxane, etc. Such materials are well known to those skilled in the art.

The compatibilizers of this invention are useful in compatibilizing polymer systems which contain two or more dissimilar crosslinking systems. In order to achieve a final, cured polymer product which exhibits the advantages of each polymer component, crosslinking between the components is necessary. However, in situations where one polymer crosslinks by a hydrosilation or free radical addition reaction and a second polymer reacts by a condensation reaction, the two polymers will not react with each other. The resulting polymer, therefore, tends to have regions where it is rich in the first polymer component and deficient in the second.

By the use of the compatibilizers of this invention, the reaction mechanism of one of the polymer components may be adapted to react with the other polymer component. Thus, the compatibilizer may be reacted with the polymer component that crosslinks by condensation and yield a polymer that is now reactive with a free radical addition reaction or by hydrosilation.

The compatibilizers of this invention also compatibilize the polymer components by leading to more effective blending between the two phases by improving the miscibility of the organic material within the silicone phase.

The following example is offered to illustrate the process for producing the compatibilizers of this invention and should not be read as limiting the scope of the invention.

EXAMPLE 1

To 1,3-(bis)gamma aminopropyl tetramethyldisiloxane was added 1,3-divinyl tetramethyldisiloxane in a 1:1 molar ratio in the presence of a catalytic amount of tetramethyl ammonium hydroxide. After equilibration there was a 50% yield of 1-(gamma amino)propyl-3-vinyl tetramethyldisiloxane. This was isolated by fractional distillation to 95% purity.

The reaction is shown as follows:

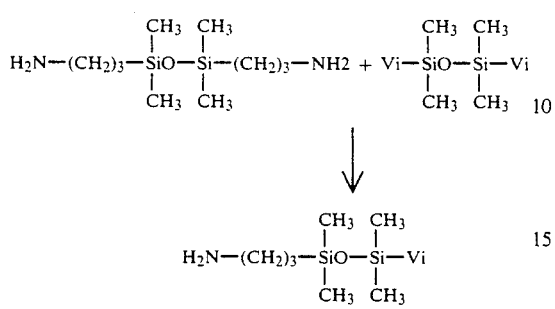

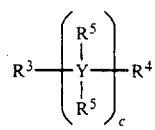

plus the starting materials in a 2:1:1 molar ratio.

What is claimed is:

1. A compatibilizer comprised of a linear molecule represented by the general formula:

$$R^3 \text{---} \left( \begin{array}{c} R^5 \\ | \\ Y \\ | \\ R^5 \end{array} \right)_c \text{---} R^4$$

wherein $R^3$ is $C_{2-12}$ alkenyl; $R^4$ is a $C_{1-10}$ alkylamine; $R^5$ is selected from the class consisting of hydrogen and $C_{1-12}$ alkyl; —$(R_2^5Y)$— is a difunctional siloxane group or a difunctional alkylene or oxyalkylene group, and "c" a number from 1 to about 100.

2. The compatibilizer according to claim 1 wherein the compatibilizer is represented by the formula:

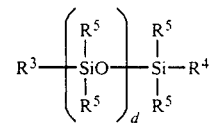

wherein $R^3$ is $C_{2-12}$ alkenyl; $R^4$ is a $C_{1-10}$ alkylamine; $R^5$ is selected from the class consisting of hydrogen and $C_{1-12}$ alkyl; and "d" is a number from 1 to about 99.

3. The compatibilizer of claim 2 wherein $R^3$ is vinyl.

4. The compatibilizer of claim 1 wherein $R^4$ is propylamine.

5. The compatibilizer of claim 2 wherein "d" is 1.

6. The compatibilizer of claim 2 wherein "d" is a number ranging from 1 to about 30.

7. The compatibilizer of claim 6 wherein "d" is a number ranging from 9 to about 12.

8. A process for producing a compatibilizer comprising the step of equilibrating bis(aminoalkyl)disoloxanes with divinyltetramethyldisiloxane in the presence of tetraalkylammonium hydroxide.

* * * * *